United States Patent
Levine et al.

(10) Patent No.: US 8,425,451 B2
(45) Date of Patent: Apr. 23, 2013

(54) GASTROINTESTINAL ANCHOR COMPLIANCE

(75) Inventors: Andy H. Levine, Newton, MA (US); David A. Melanson, Hudson, NH (US)

(73) Assignee: GI Dynamics, Inc., Lexington, MA (US)

( * ) Notice: Subject to any disclaimer, the term of this patent is extended or adjusted under 35 U.S.C. 154(b) by 62 days.

(21) Appl. No.: 13/151,983

(22) Filed: Jun. 2, 2011

(65) Prior Publication Data
US 2011/0301523 A1    Dec. 8, 2011

Related U.S. Application Data

(63) Continuation of application No. 11/147,992, filed on Jun. 8, 2005, now Pat. No. 7,976,488.

(51) Int. Cl.
*A61M 5/00* (2006.01)
*A61F 2/04* (2006.01)
*A61F 2/90* (2006.01)
*A61F 2/94* (2006.01)

(52) U.S. Cl.
USPC ......... 604/8; 623/23.65; 623/23.64; 623/23.7

(58) Field of Classification Search ............... 623/23.64, 623/23.65, 23.7; 604/8
See application file for complete search history.

(56) References Cited

U.S. PATENT DOCUMENTS

| | | | |
|---|---|---|---|
| 1,899,781 A | 2/1933 | Twiss | |
| 2,464,933 A | 3/1949 | Kaslow | |
| 3,780,740 A | 12/1973 | Rhea | |
| 4,133,315 A | 1/1979 | Berman et al. | |

(Continued)

FOREIGN PATENT DOCUMENTS

| DE | 33 26 061 A1 | 2/1984 |
|---|---|---|
| EP | 0 480 667 B1 | 4/1992 |

(Continued)

OTHER PUBLICATIONS

Bethge, N., et al., "Human tissue responses to metal stents implanted in vivo for the palliation of malignant stenoses," *Gastrointestinal Endoscopy* 43(6):596/602 (1996).

(Continued)

*Primary Examiner* — Susan Su
(74) *Attorney, Agent, or Firm* — Hamilton, Brook, Smith & Reynolds, P.C.

(57) ABSTRACT

A collapsible gastrointestinal anchor can be characterized in various embodiments by a radial force of about 0.1 Newtons (N) or greater at a compressed diameter of 25 millimeters (mm); by an average spring rate of about 13 Newtons/meter (N/m) or greater in a range of motion between a relaxed diameter and a compressive elastic deformation diameter; or by a radial force over the range of motion of about 0.1 N or greater. Typically, the anchor can be adapted to be retained within a subject's intestine, more typically in the duodenum, or particularly in the duodenal bulb just distal to the pylorus. A gastrointestinal implant device includes the collapsible gastrointestinal anchor and a floppy sleeve. The sleeve is open at both ends and adapted to extend into a subject's intestine, the anchor being coupled to a proximal portion of the sleeve. Also include are methods of implanting the gastrointestinal implant device in a subject, and methods of treating a subject for disease.

The disclosed gastrointestinal invention leads to an improved ability to secure anchors and devices in the gastrointestinal tract while tending to minimize migration.

12 Claims, 13 Drawing Sheets

U.S. PATENT DOCUMENTS

| | | |
|---|---|---|
| 4,134,405 A | 1/1979 | Smit |
| 4,246,893 A | 1/1981 | Berson |
| 4,265,694 A | 5/1981 | Boretos et al. |
| 4,270,542 A | 6/1981 | Plumley |
| 4,271,827 A | 6/1981 | Angelchik |
| 4,279,251 A | 7/1981 | Rüsch |
| 4,315,509 A | 2/1982 | Smit |
| 4,341,218 A | 7/1982 | Ü |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,823,808 A | 4/1989 | Clegg et al. |
| 4,830,003 A * | 5/1989 | Wolff et al. ............... 606/191 |
| 4,846,836 A | 7/1989 | Reich |
| 4,878,905 A | 11/1989 | Blass |
| 4,905,693 A | 3/1990 | Ravo |
| 4,913,141 A | 4/1990 | Hillstead |
| 5,035,706 A | 7/1991 | Giantureo et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,102,417 A * | 4/1992 | Palmaz ............... 606/195 |
| 5,104,399 A | 4/1992 | Lazarus |
| 5,123,917 A | 6/1992 | Lee |
| 5,135,516 A | 8/1992 | Sahatjian et al. |
| 5,152,756 A | 10/1992 | Quinn et al. |
| 5,152,782 A | 10/1992 | Kowligi et al. |
| 5,176,617 A | 1/1993 | Fischell et al. |
| 5,190,561 A | 3/1993 | Graber |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,423,851 A | 6/1995 | Samuels |
| 5,443,498 A | 8/1995 | Fontaine |
| 5,456,713 A | 10/1995 | Chuter |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,713 A | 9/1997 | Andersen et al. |
| 5,665,064 A | 9/1997 | Bodicky et al. |
| 5,669,932 A | 9/1997 | Fischell et al. |
| 5,690,642 A | 11/1997 | Osborne et al. |
| 5,693,084 A | 12/1997 | Chuter |
| 5,695,516 A | 12/1997 | Fischell et al. |
| 5,697,971 A | 12/1997 | Fischell et al. |
| 5,713,948 A | 2/1998 | Uflacker |
| 5,715,832 A | 2/1998 | Koblish et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,735,892 A | 4/1998 | Myers et al. |
| 5,743,874 A | 4/1998 | Fischell et al. |
| 5,749,825 A | 5/1998 | Fischell et al. |
| 5,755,777 A | 5/1998 | Chuter |
| 5,759,174 A | 6/1998 | Fischell et al. |
| 5,776,186 A | 7/1998 | Uflacker |
| 5,792,144 A | 8/1998 | Fischell et al. |
| 5,792,172 A | 8/1998 | Fischell et al. |
| 5,800,456 A | 9/1998 | Maeda et al. |
| 5,800,526 A | 9/1998 | Anderson et al. |
| 5,820,584 A | 10/1998 | Crabb |
| 5,830,229 A | 11/1998 | Konya et al. |
| 5,840,009 A | 11/1998 | Fischell et al. |
| 5,843,164 A | 12/1998 | Frantzen et al. |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,910,145 A | 6/1999 | Fischell et al. |
| 5,913,895 A | 6/1999 | Burpee et al. |
| 5,919,233 A | 7/1999 | Knopf et al. |
| 5,925,063 A | 7/1999 | Khosravi |
| 5,962,620 A | 10/1999 | Reich et al. |
| 5,964,771 A | 10/1999 | Beyar et al. |
| 5,976,153 A | 11/1999 | Fischell et al. |
| 6,013,019 A | 1/2000 | Fischell et al. |
| 6,027,508 A | 2/2000 | Ren et al. |
| 6,027,526 A | 2/2000 | Limon et al. |
| 6,035,856 A | 3/2000 | LaFontaine et al. |
| 6,074,673 A | 6/2000 | Guillen |
| 6,086,604 A | 7/2000 | Fischell et al. |
| 6,099,552 A | 8/2000 | Adams |
| 6,102,887 A | 8/2000 | Altman |
| 6,106,642 A | 8/2000 | DiCarlo et al. |
| 6,120,533 A | 9/2000 | Fischell |
| 6,132,471 A | 10/2000 | Johlin, Jr. |
| 6,146,323 A | 11/2000 | Fischell |
| 6,146,416 A | 11/2000 | Andersen et al. |
| 6,152,956 A | 11/2000 | Pierce |
| 6,179,868 B1 | 1/2001 | Burpee et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,241,738 B1 | 6/2001 | Dereume |
| 6,241,757 B1 | 6/2001 | An et al. |
| 6,251,064 B1 | 6/2001 | Silverman et al. |
| 6,251,132 B1 | 6/2001 | Ravenscroft et al. |
| 6,270,521 B1 | 8/2001 | Fischell et al. |
| 6,270,524 B1 * | 8/2001 | Kim ............... 623/1.15 |
| 6,293,960 B1 | 9/2001 | Ken |
| 6,302,891 B1 | 10/2001 | Nadal |
| 6,302,917 B1 | 10/2001 | Dua et al. |
| 6,315,708 B1 | 11/2001 | Salmon et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,355,056 B1 | 3/2002 | Pinheiro |
| 6,356,782 B1 | 3/2002 | Sirimanne et al. |
| 6,375,660 B1 | 4/2002 | Fischell et al. |
| 6,383,214 B1 | 5/2002 | Banas et al. |
| 6,387,114 B2 | 5/2002 | Adams |
| 6,401,718 B1 | 6/2002 | Johnson et al. |
| 6,406,792 B1 | 6/2002 | Briquet et al. |
| 6,428,558 B1 | 8/2002 | Jones et al. |
| 6,450,989 B2 | 9/2002 | Dubrul et al. |
| 6,458,074 B1 | 10/2002 | Matsui et al. |
| 6,485,409 B1 | 11/2002 | Voloshin et al. |
| 6,485,515 B2 | 11/2002 | Strecker |

| Patent | Date | Inventor |
|---|---|---|
| 6,508,833 B2 | 1/2003 | Pavcnik et al. |
| 6,520,985 B1 | 2/2003 | Burpee et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,537,247 B2 | 3/2003 | Shannon |
| 6,540,775 B1 | 4/2003 | Fischell et al. |
| 6,540,789 B1 | 4/2003 | Silverman et al. |
| 6,544,291 B2 | 4/2003 | Taylor |
| 6,547,817 B1 | 4/2003 | Fischell et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,589,213 B2 | 7/2003 | Reydel |
| 6,589,275 B1 | 7/2003 | Ivancev et al. |
| 6,623,518 B2 | 9/2003 | Thompson et al. |
| 6,635,069 B1 | 10/2003 | Teoh et al. |
| 6,635,079 B2 | 10/2003 | Unsworth et al. |
| 6,645,239 B1 | 11/2003 | Park et al. |
| 6,652,555 B1 | 11/2003 | VanTassel et al. |
| 6,652,582 B1 | 11/2003 | Stinson |
| 6,656,194 B1 | 12/2003 | Gannoe et al. |
| 6,669,722 B2 | 12/2003 | Chen et al. |
| 6,675,809 B2 | 1/2004 | Stack et al. |
| 6,676,692 B2 | 1/2004 | Rabkin et al. |
| 6,695,875 B2 | 2/2004 | Stelter et al. |
| 6,699,263 B2 | 3/2004 | Cope |
| 6,699,278 B2 | 3/2004 | Fischell et al. |
| 6,706,061 B1 | 3/2004 | Fischell et al. |
| 6,716,240 B2 | 4/2004 | Fischell et al. |
| 6,736,840 B2 | 5/2004 | Fischell et al. |
| 6,740,121 B2 | 5/2004 | Geitz |
| 6,755,869 B2 | 6/2004 | Geitz |
| 6,773,440 B2 | 8/2004 | Gannoe et al. |
| 6,776,791 B1 | 8/2004 | Stallings et al. |
| 6,802,868 B2 | 10/2004 | Silverman et al. |
| 6,821,291 B2 | 11/2004 | Bolea et al. |
| 6,845,776 B2 | 1/2005 | Stack et al. |
| 6,936,065 B2 | 8/2005 | Khan et al. |
| 6,960,233 B1 | 11/2005 | Berg et al. |
| 7,011,673 B2 | 3/2006 | Fischell et al. |
| 7,025,791 B2 | 4/2006 | Levine et al. |
| 7,033,384 B2 | 4/2006 | Gannoe et al. |
| 7,037,327 B2 | 5/2006 | Salmon et al. |
| 7,037,344 B2 | 5/2006 | Kagan et al. |
| 7,087,088 B2 | 8/2006 | Berg et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,211,114 B2 | 5/2007 | Bessler |
| 7,220,237 B2 | 5/2007 | Gannoe et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,329,285 B2 | 2/2008 | Levine et al. |
| 7,338,520 B2 | 3/2008 | Bailey et al. |
| 7,347,875 B2 | 3/2008 | Levine et al. |
| 7,354,454 B2 | 4/2008 | Stack et al. |
| 7,476,256 B2 | 1/2009 | Meade et al. |
| 2001/0020190 A1 | 9/2001 | Taylor |
| 2002/0022853 A1 | 2/2002 | Swanson et al. |
| 2002/0032487 A1 | 3/2002 | Dua et al. |
| 2002/0055771 A1 | 5/2002 | Sandock |
| 2002/0065545 A1 | 5/2002 | Leonhardt et al. |
| 2002/0091439 A1 | 7/2002 | Baker et al. |
| 2002/0120277 A1 | 8/2002 | Hauschild et al. |
| 2002/0143387 A1 | 10/2002 | Soetikno et al. |
| 2002/0147489 A1 | 10/2002 | Hong et al. |
| 2002/0151953 A1 | 10/2002 | Chobotov et al. |
| 2002/0177890 A1 | 11/2002 | Lenker |
| 2002/0183768 A1 | 12/2002 | Deem et al. |
| 2002/0183786 A1 | 12/2002 | Girton |
| 2002/0188344 A1 | 12/2002 | Bolea et al. |
| 2002/0193828 A1 | 12/2002 | Griffin et al. |
| 2003/0032941 A1 | 2/2003 | Boyle et al. |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0233140 A1 | 12/2003 | Hartley et al. |
| 2004/0019388 A1 | 1/2004 | Starkebaum |
| 2004/0024386 A1 | 2/2004 | Deem et al. |
| 2004/0037865 A1 | 2/2004 | Miller |
| 2004/0039452 A1 | 2/2004 | Bessler |
| 2004/0044357 A1 | 3/2004 | Gannoe et al. |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0098079 A1 | 5/2004 | Hartley et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122470 A1 | 6/2004 | Deem et al. |
| 2004/0133147 A1 | 7/2004 | Woo |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172088 A1 | 9/2004 | Knudson et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0204768 A1 | 10/2004 | Geitz |
| 2004/0210243 A1 | 10/2004 | Gannoe et al. |
| 2004/0220682 A1 | 11/2004 | Levine et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267533 A1 | 12/2005 | Gertner |
| 2006/0009858 A1 | 1/2006 | Levine et al. |
| 2006/0064120 A1 | 3/2006 | Levine et al. |

| | | | |
|---|---|---|---|
| 2006/0106332 A1 | 5/2006 | Knudson et al. | |
| 2006/0155312 A1 | 7/2006 | Levine et al. | |
| 2006/0161139 A1 | 7/2006 | Levine et al. | |
| 2006/0161172 A1 | 7/2006 | Levine et al. | |
| 2006/0161187 A1 | 7/2006 | Levine et al. | |
| 2006/0161265 A1 | 7/2006 | Levine et al. | |
| 2006/0212042 A1 | 9/2006 | Lamport et al. | |
| 2006/0265082 A1 | 11/2006 | Meade et al. | |
| 2007/0027548 A1 | 2/2007 | Levine et al. | |
| 2007/0032879 A1 | 2/2007 | Levine et al. | |
| 2007/0049801 A1 | 3/2007 | Lamport et al. | |
| 2007/0083271 A1 | 4/2007 | Levine et al. | |
| 2007/0183613 A1 | 8/2007 | Juneau et al. | |
| 2008/0071383 A1 | 3/2008 | Levine et al. | |
| 2008/0097466 A1 | 4/2008 | Levine et al. | |
| 2008/0103604 A1 | 5/2008 | Levine et al. | |
| 2008/0208357 A1 | 8/2008 | Melanson et al. | |
| 2008/0223476 A1 | 9/2008 | Stinson | |
| 2008/0234834 A1 | 9/2008 | Meade et al. | |

FOREIGN PATENT DOCUMENTS

| | | | |
|---|---|---|---|
| EP | 0278937 B1 | 10/1993 | |
| EP | 0 506 918 B1 | 1/1996 | |
| EP | 0754017 B1 | 1/1997 | |
| EP | 0843538 B1 | 5/1998 | |
| EP | 0 857 471 A2 | 8/1998 | |
| EP | 0935977 A2 | 8/1999 | |
| EP | 0935977 A3 | 8/1999 | |
| EP | 1 481 649 A1 | 12/2004 | |
| EP | 1 504 778 A2 | 2/2005 | |
| EP | 1 504 778 A3 | 2/2005 | |
| JP | 04212348 | 8/1992 | |
| WO | WO 92/06734 A1 | 4/1992 | |
| WO | WO 95/05132 | 2/1995 | |
| WO | WO 97/03624 A1 | 2/1997 | |
| WO | WO 98/22045 | 5/1998 | |
| WO | WO 99/23953 | 5/1999 | |
| WO | WO 99/44536 | 9/1999 | |
| WO | WO 00/12027 | 3/2000 | |
| WO | WO 00/28922 A1 | 5/2000 | |
| WO | WO 00/32137 | 6/2000 | |
| WO | WO 00/42945 A1 | 7/2000 | |
| WO | WO 00/42949 | 7/2000 | |
| WO | WO 01/12256 A1 | 2/2001 | |
| WO | WO 01/35861 A1 | 5/2001 | |
| WO | WO 01/45485 A2 | 6/2001 | |
| WO | WO 02/081019 A1 | 10/2002 | |
| WO | WO 02/096327 A2 | 12/2002 | |
| WO | WO 03/017882 A2 | 3/2003 | |
| WO | WO 03/086246 A1 | 10/2003 | |
| WO | WO 03/086247 A1 | 10/2003 | |
| WO | WO 03/086360 A1 | 10/2003 | |
| WO | WO 03/094785 A1 | 11/2003 | |
| WO | WO 2004/000169 A1 | 12/2003 | |
| WO | WO 2004/004542 A2 | 1/2004 | |
| WO | WO 2004/004542 A3 | 1/2004 | |
| WO | WO 2004/014237 A1 | 2/2004 | |
| WO | WO 2004/019765 A2 | 3/2004 | |
| WO | WO 2004/019765 A3 | 3/2004 | |
| WO | WO 2004/021894 A1 | 3/2004 | |
| WO | WO 2004/037064 A2 | 5/2004 | |
| WO | WO 2004/037064 A3 | 5/2004 | |
| WO | WO 2004/049982 A2 | 6/2004 | |
| WO | WO 2004/064680 A1 | 8/2004 | |
| WO | WO 2004/064682 A1 | 8/2004 | |
| WO | WO 2004/064685 A1 | 8/2004 | |
| WO | WO 2004/069331 A2 | 8/2004 | |
| WO | WO 2004/069332 A1 | 8/2004 | |
| WO | WO 2004/073782 A1 | 9/2004 | |
| WO | WO 2004/087014 A2 | 10/2004 | |
| WO | WO 2004/087233 A2 | 10/2004 | |
| WO | WO 2004/093639 A2 | 11/2004 | |
| WO | WO 2004/093639 A3 | 11/2004 | |
| WO | WO 2005/011533 A2 | 2/2005 | |
| WO | WO 2005/060869 A1 | 7/2005 | |
| WO | WO 2005/060882 A1 | 7/2005 | |
| WO | WO 2005/082296 A1 | 9/2005 | |
| WO | WO 2005/110280 A2 | 11/2005 | |
| WO | WO 2005/110280 A3 | 11/2005 | |
| WO | WO 2005/117716 A2 | 12/2005 | |
| WO | WO 2005/118049 A1 | 12/2005 | |
| WO | WO 2005/120363 A1 | 12/2005 | |
| WO | WO 2006/016894 A1 | 2/2006 | |
| WO | WO 2006/034062 A1 | 3/2006 | |
| WO | WO 2006/078781 A1 | 7/2006 | |
| WO | WO 2006/078927 A1 | 7/2006 | |
| WO | WO 2006/088578 A1 | 8/2006 | |
| WO | WO 2006/102012 A1 | 9/2006 | |
| WO | WO 2006/133311 A2 | 12/2006 | |

OTHER PUBLICATIONS

Binkert, C. A., et al., "Benign and Malignant Stenoses of the Stomach and Duodenum: Treatment with Self/expanding Metallic Endoprostheses," *Radiology* 199(2):335/338 (1996).

Choostent™, Covered Esophageal Stent, Instructions, Retrieved from the Internet (http://mitech.co.kr/uploads/images/282/use guide esophachoo_english.pdf) on Jul. 26, 2005.

Cwikiel, W., et al., "Self/expanding Stent in the Treatment of Benign Esophageal Strictures: Experimental Study in Pigs and Presentation of Clinical Cases," *Radiology* 187(3):667/671 (1993).

Dolan, K. et al., "Treating Diabetes in the Morbidly Obese by Laproscopic Gastric Band," *Obesity Surgery*, vol. 13, pp. 439/443 (2003).

Dormann, A.J. et al., "Self/expanding metallic stents for continous dilatation of benign stenosis in gastrointestinal tract / first results of long/term follow/up in interim stent application in pyloric and colonic obstructions," *Z Gastroenteral* 39:957/960 (2001).

Feretis, C., et al., "Palliation of Malignant Gastric Outlet Obstruction with Self/Expanding Metal Stents," Endoscopy 28:225/228 (1996).

Hwang, J.C., et al., "Covered Retrievable Tracheobronchial Hinged Stent: An Experimental Study in Dogs," *J. Vase. Interv. Radiol.*, 12(12):1429/1436 (Dec. 2001).

International Search Report from related application PCT/US2008/013540 mailed on Mar. 26, 2009.

Irie, T., et al., "Relocatable Gianturco Expandable Metallic Stents[1]," *Radiology*, 178:575/578 (1991).

Lee, B.H., et al., "New Self/Expandable Spiral Metallic Stent: Pre-liminary clinical Evaluation in Malignant Biliary Obstruction," *J. Vase Intery Radiol.*, 6(4):635/640 (Jul. 8, 1995).

Lee, S.H., "The Role of Oesophageal Stenting in the Non/Surgical Management of Oesophageal Strictures," *British J. Radiology*, 74:891/900 (Oct. 2001).

Notification Concerning Transmittal of International Preliminary Report on Patentability for Int'l Application No. PCT/US2006/022168; Date Mailed: Dec. 27, 2007.

Notification of Transmittal of the International Search Report and the Written Opinion of the International Searching Authority for Int'l Application No. PCT/US2006/022168; Date Mailed: Dec. 6, 2006.

Park, B.P. et al., Malignant Obstruction of Gastric Outlet and Duodenum: Palliation with Flexible Covered Metallic Stents, *Radiology* 219(3):679/683 (2001).

Parodi, J.C., M.D., "Endovascular Repair of Abdominal Aortic Aneu-rysms," *Advances in Vascular Surgery*, vol. 1, pp. 85/105 (1993).

Pories, W.J., "Why Does the Gastric Bypass Control Type 2 Diabetes Mellitus?" *Obesity Surgery*, 2:303/313 (1992).

Pories, W.J., et al., "Etiology of Type II Diabetes Mellitus: Role of the Foregut," *World J. Surg.*, 25:527/531 (2001).

Rubino, F. and J. Marescaux, "Effect of Duodenal/Jejunal Exclusion in a Non/obese Animal Model of Type 2 Diabetes, A New Perspective for an Old Disease," *Annals of Surgery* 239(1):1/11 (2004).

Rubino, F., et al., "Potential of Surgery for Curing Type 2 Diabetes Mellitus," *Annals of Surgery* 236(5): 554/559 (2002).

Sandha, G. S. and Marcon, N. E., "Expandable Metal Stents for Benign Esophageal Obstruction," Gastrointestinal Endoscopy Clinics of North America 9:(3)437/446 (1999).

Shim, C.S., et al., "Fixation of a Modified Covered Esophageal Stent: Its Clinical Usefulness for Preventing Stent Migration," *Endoscopy*, 33(10):843/848 (Oct. 2001).

Song, H.Y., et al., "Benign and Malignant Esophageal Strictures: Treatment with a Polyurethane/Covered Retrievable Expandable Metallic Stent[1]," *Radiology*, 203(3):747/752 (Jun. 1997).

Song, H.Y., et al., "Covered Retrievable Expandable Nitinol Stents in Patients with Benign Esophageal Strictures: Initial Experience[1]," *Radiology*, 217:551/557 (Nov. 2000).

Song, H.Y., et al., "Tracheobronchial Strictures: Treatment with a Polyurethane/Covered Retrievable Expandable Nitinol Stent / Initial Experience," *Radiology*, 213:905/912 (Dec. 1999).

Written Opinion of the International Searching Authority from related application PCT/US2008/013540 mailed on Mar. 26, 2009.

Yates III, M. R., et al., "Palliation of Malignant Gastric and Small Intestinal Strictures With Self/Expandable Metal Stents," *Endoscopy* 30:266/272 (1998).

Yoon, C.J., et al., "Removal of Retrievable Esophageal and Gastrointestinal Stents: Experience in 113 Patients," *American J. of Roentgenology*, 183:1437/1444 (Nov. 2004).

Keet, A.D, *The Pyloric Sphincteric Cylinder in Health and Disease*, Springer-Verlag, New York, Chapter 11, p. 44, http://med.plig.org/11, printed from the Internet on Nov. 6, 2009.

* cited by examiner

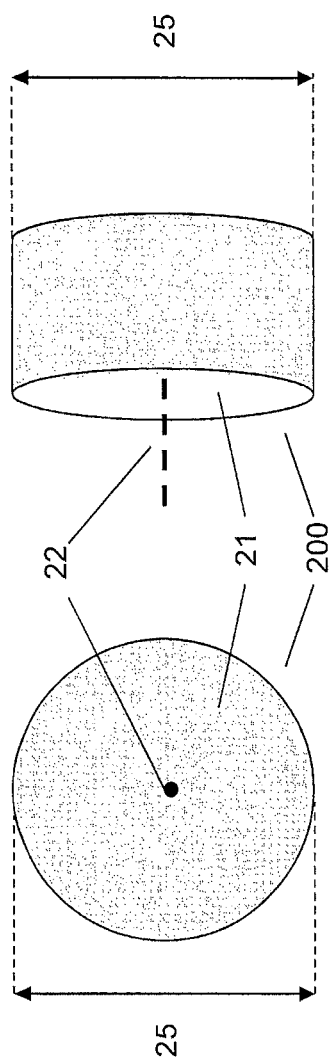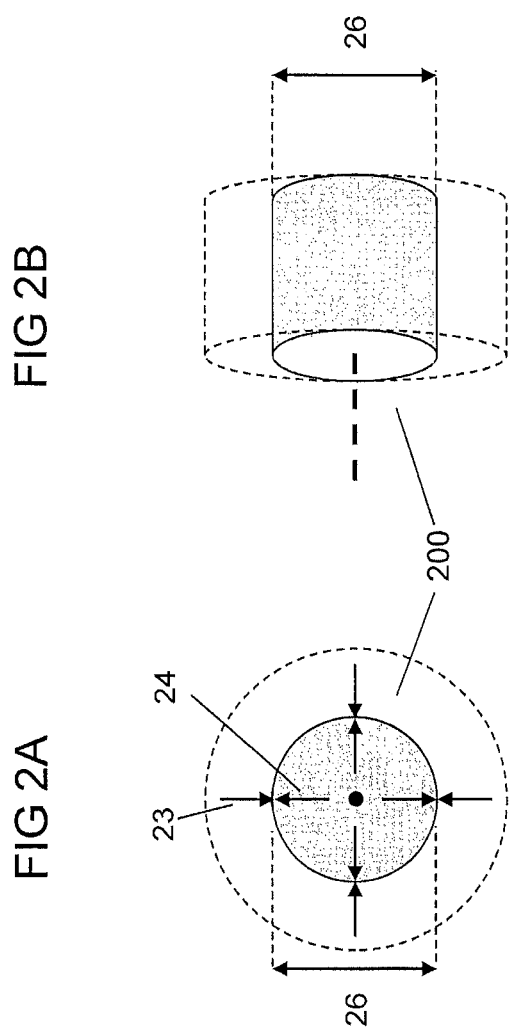

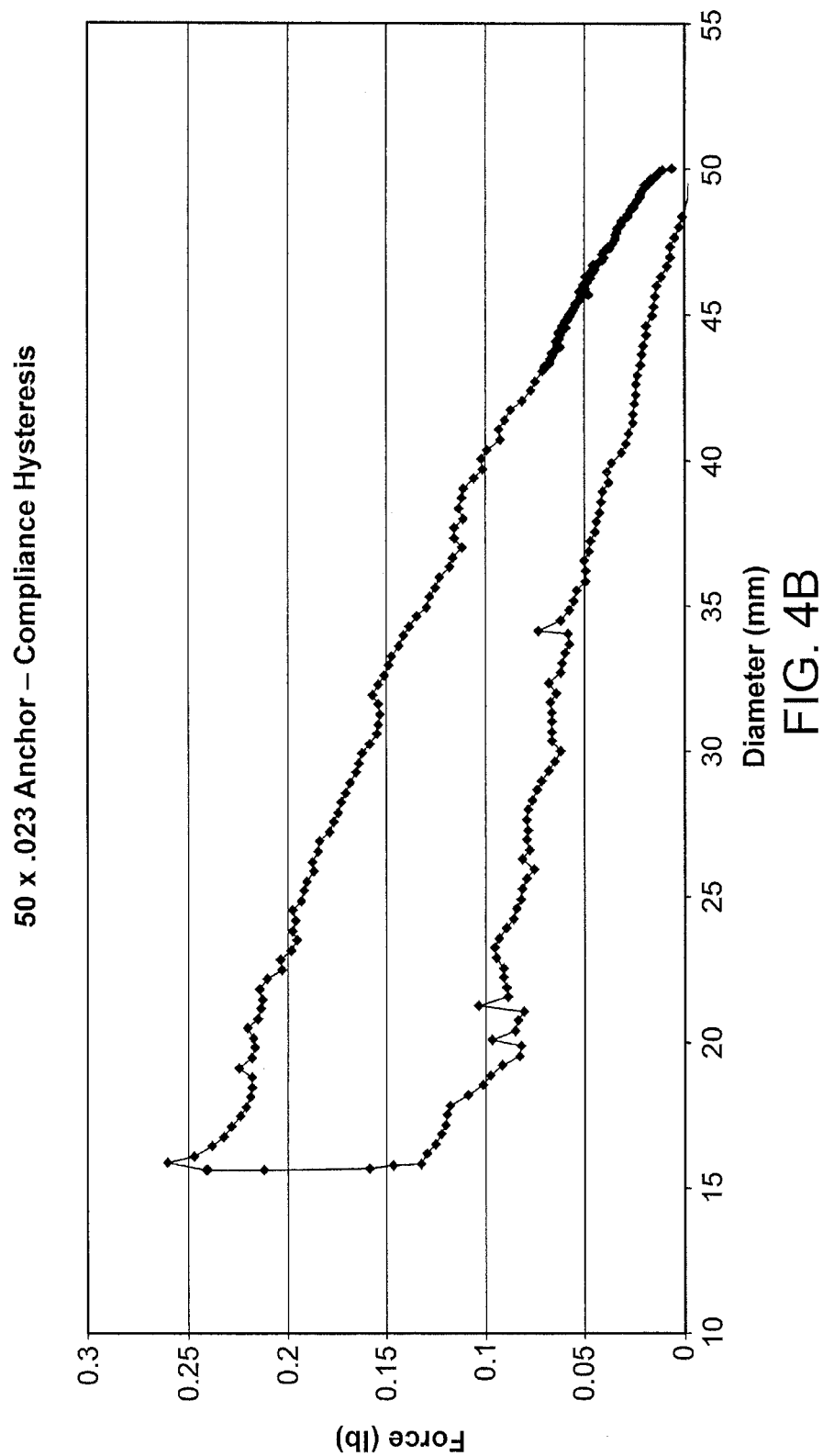

GASTROINTESTINAL ANCHOR COMPLIANCE

RELATED APPLICATION

This application is a continuation of U.S. application Ser. No. 11/147,992, filed Jun. 8, 2005 now U.S. Pat. No. 7,976,488. The entire teachings of the above application are incorporated herein by reference.

BACKGROUND OF THE INVENTION

According to the Center for Disease Control (CDC), over sixty percent of the United States population is overweight, and almost twenty percent are obese, presenting an overwhelming health problem. Moreover, obesity-related conditions cause as many as 280,000 deaths per year, generate $51 billion in annual US healthcare costs, and cause Americans to spend $33 billion per year on weight loss products. For example, one of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Two common surgical procedures that produce long-term weight loss are the Roux-en-Y gastric bypass and the biliopancreatic diversion with duodenal switch (BPD). Both procedures reduce the size of the stomach and shorten the effective-length of intestine available for digestion and nutrient absorption. However, these are surgical procedures with significant side effects, and thus they are reserved for the most morbidly obese.

Other devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices are yet to be successfully implemented.

Examples of gastrointestinal sleeves have been described for treating obesity while minimizing the risks of surgery (See, for example, Meade et al, U.S. Utility application Ser. No. 10/858,851, filed Jun. 1, 2004; the entire teachings of which are incorporated herein by reference). Further improvements are desired to more fully realize the advantages which can be provided by gastrointestinal sleeves in treating obesity.

SUMMARY OF THE INVENTION

There is still a need for improved anchors to secure gastrointestinal sleeves in the gastrointestinal tract. Moreover, there is a need for gastrointestinal implant devices with improved anchors, and methods of treatment therewith.

The invention is a collapsible gastrointestinal anchor. Typically, the anchor can be adapted to be retained within the intestine of a subject, more typically within the duodenum, or particularly in the duodenal bulb just distal to the pylorus.

A gastrointestinal implant device includes the collapsible gastrointestinal anchor and a floppy sleeve. The sleeve is open at both ends and adapted to extend into the intestine of a subject distal to the anchor, the anchor being coupled to a proximal portion of the sleeve. Typically, the sleeve can be adapted to extend into the duodenum, or in some embodiments into the jejunum.

In various embodiments, the anchor is characterized by a radial force of about 0.1 Newtons (N) or greater at a compressed diameter of 25 millimeters (mm). Typically, the radial force at 25 mm compression can be about 0.3 N or greater, more typically about 0.4 N or greater, or particularly between about 0.5 N and about 1.5 N.

In various embodiments, the anchor is characterized by an average spring rate of about 13 Newtons/meter (N/m) or greater in a range of motion, the range of motion being within a diameter range defined by a relaxed diameter and a compressive elastic deformation diameter. More particularly, the average value of the spring rate is between about 15 N/m and about 35 N/m. In some embodiments, the spring rate is substantially constant over the range of motion, or in other words, the force versus displacement data is substantially linear over the range of motion.

In various embodiments, the anchor is characterized by a radial force over the range of motion of about 0.1 N or greater, typically, about 0.2 N or greater, more typically, about 0.3 N or greater, or particularly about 0.4 N or greater.

In some embodiments, the range of motion can be about 20 mm or greater, more typically about 30 mm or greater, or particularly about 35 mm or greater. In some embodiments, the range of motion can be a percentage of the relaxed diameter of the anchor of about 30% or greater.

In various embodiments, the anchor is characterized by a relaxed diameter. Generally, the relaxed diameter can be about 40 mm or greater, typically, about 45 mm or greater, or more typically, between about 45 mm and about 65 mm. In particular embodiments, the relaxed diameter can be about 50 mm or about 60 mm.

In various embodiments, the anchor can be characterized by the radial force being about 0.4 N or less at a diameter of 55 mm, typically at a diameter of 50 mm, more typically at a diameter of 45 mm, or particularly at a diameter of 40 mm. In various embodiments, the anchor can be characterized by the radial force being about 0.3 N or less at a diameter of 55 mm, typically at a diameter of 50 mm, more typically at a diameter of 45 mm, or particularly at a diameter of 40 mm. In various embodiments, the anchor can be characterized by the radial force being about 0.2 N or less at a diameter of 55 mm, typically at a diameter of 50 mm, more typically at a diameter of 45 mm, or particularly at a diameter of 40 mm.

Anchors exhibiting hysteresis can have two radial force values for a given displacement, one measured during the loading (compression) and one measured during unloading (expansion). Generally, the characterizing of radial force values (the radial force at 25 mm, radial force over the range of motion, spring rate) can be met in either loading or unloading. However, it is preferred that such values be met while unloading the anchor from a compressed state.

The anchor can be characterized by a compressive elastic deformation diameter which can be expressed in absolute or relative terms. In various embodiments, the compressive elastic deformation diameter is about 12 mm or less, or particularly about 8 mm or less. In various embodiments, the compressive elastic deformation diameter is a percentage of the relaxed diameter of about 30% or less, more typically about 20% or less.

In various embodiments, the anchor can be in the form of a ring, a stent formed by a network of struts, or a wave spring. Typically, the anchor can be a wave spring. The anchor can be made of any elastic material which can be formed into an anchor with the disclosed characteristics. For example, the anchor can be made of a material such as heat-treated spring steel, stainless steel, Nitinol, nickel-cobalt-chromium-molybdenum alloy, a polymer, a composite, or the like. Typically, the anchor can be made of Nitinol wire.

In various embodiments, the anchor includes attaching means adapted to secure the anchor to the intestine. The attaching means can include an interference fit, chemical fasteners, mechanical fasteners, or the like. Mechanical fasteners can include, for example, sutures, surgical staples, barbs, or the like. In various embodiments, the anchor includes barbs that extend from the exterior surface of the anchor. In particular embodiments, the barbs extend from the surface exterior surface of the anchor by about 2 mm or greater. In various embodiments, the method includes securing the proximal portion of the sleeve through the intestine in the subject with the barbs.

A method of treating a subject includes the steps of securing the gastrointestinal implant device within a subject's intestine and extending a distal end of the sleeve through the subject's intestine. In various embodiments, the subject can be treated for a disease such as obesity or Type-II diabetes.

A method of implanting the gastrointestinal implant device includes introducing the gastrointestinal implant device into a subject's intestine, the anchor being compressed, and expanding the compressed anchor to secure the gastrointestinal implant device within the subject's intestine. In particular embodiments of the method, the anchor is compressed to about 12 mm in diameter, the anchor being characterized by a compressive elastic deformation diameter of less than the compressed diameter.

In various embodiments, the gastrointestinal implant device employed in the method of treatment can independently include any of the features disclosed herein for the gastrointestinal implant device or the anchor. Moreover, each method of treatment or implantation can include steps of operating the various features of the gastrointestinal implant device.

Particular embodiments are contemplated corresponding to each possible independent combination of the values, ranges, and features described herein for the gastrointestinal anchor, the gastrointestinal implant device, and the methods.

For example, in particular embodiments, a collapsible gastrointestinal anchor includes a wave spring having a plurality of barbs extending therefrom. Also in particular embodiments, a gastrointestinal implant device includes a flexible sleeve, open at both ends and adapted to extend into a subject's intestine, and a collapsible gastrointestinal anchor coupled to a proximal portion of the sleeve, the anchor comprising a wave spring having a plurality of barbs extending therefrom. In particular embodiments, a method of treating a subject includes the steps of securing the gastrointestinal implant device within the subject's intestine and extending the distal end of the sleeve into the subject's intestine. The wave spring for each embodiment in this paragraph is characterized by a relaxed diameter of about 40 millimeters (mm) or greater; a compressive elastic deformation diameter of about 12 mm or less; an average spring rate of about 13 Newtons/meter (N/m) or greater over a range of motion of about 20 mm or greater, the range of motion being within a diameter range defined by the relaxed diameter and the compressive elastic deformation diameter; and a radial force under compression, the radial force being about 0.3 Newtons (N) or greater at a diameter of 25 mm, and the radial force being about 0.2 N or greater over the range of motion.

The disclosed gastrointestinal invention leads to an improved ability to secure anchors and devices in the gastrointestinal tract while tending to minimize migration. The force exerted on the gastrointestinal tract is generally sufficient to hold the anchors and devices in place without damaging the gastrointestinal tissue. Moreover, because the spring rate of the anchors is compliant over the range of motion, the anchors can apply sufficient force over a range of gastrointestinal tract diameters, which leads to better retention of the anchors. Also, the radial force and spring rate are such that the radial force decreases as the diameter increases and the anchor does not tend to cause the intestine to expand or grow beyond its normal range. Further, the anchor deforms elastically within its operating range which eases compression for implantation via catheter delivery devices, and the like.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2A and 2B show anchor 200 in axial and perspective views at a relaxed diameter 25;

FIGS. 2C and 2D show anchor 200 in axial and perspective views at a compressed diameter 26;

FIG. 4B is a hysteresis plot of a 50 mm diameter by 0.023 inch thick Nitinol wave anchor.

DETAILED DESCRIPTION OF THE INVENTION

Figure 1A:
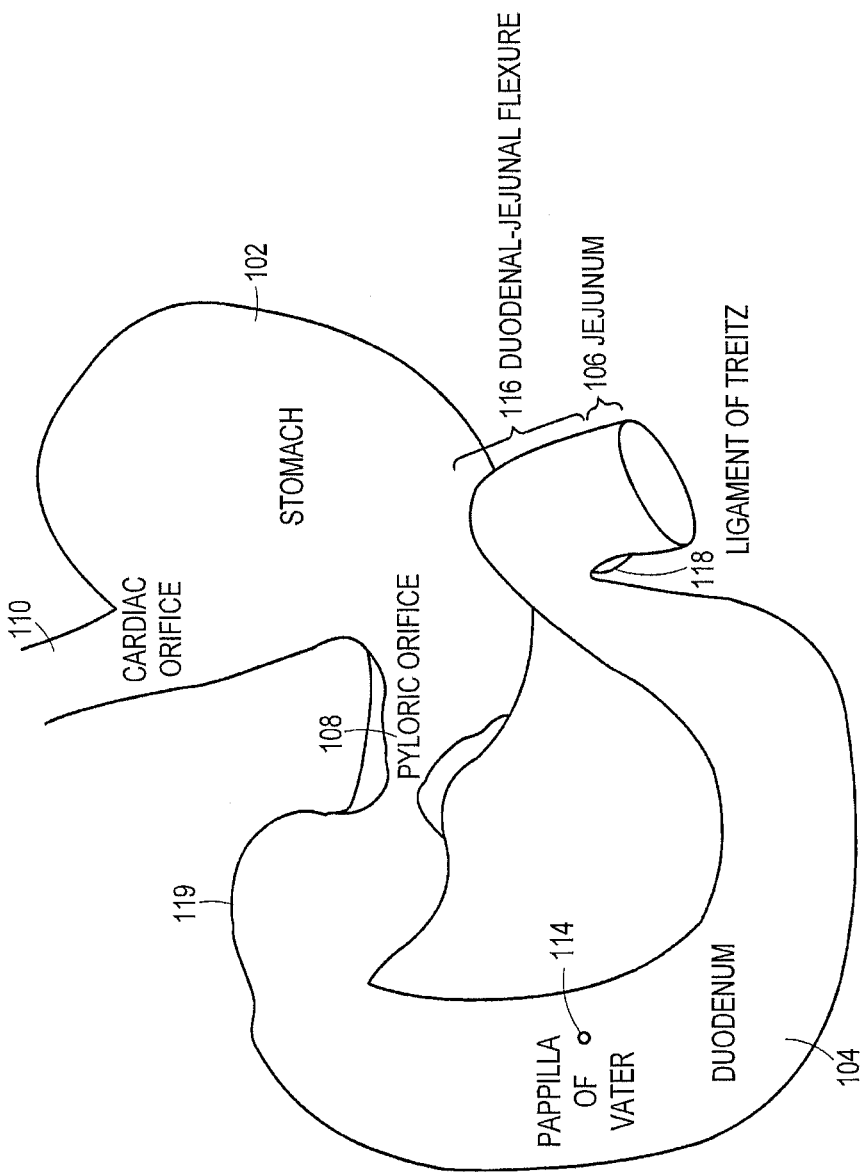
FIG. 1A is a sectional view of a portion of a digestive tract in a body.

FIG. 1A is a sectional view of a portion of a digestive tract in a body, which will be referred to in the description of preferred embodiments of the invention in subsequent sections.

Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus 108 to the ileo-caecal valve where it terminates in the large intestine. The small intestine has three sections, the duodenum 104, jejunum 106 and the ileum (not shown). The first eight to ten inch section of the small intestine 112, the duodenum 104, is the shortest, widest and most fixed part of the small intestine 112.

The duodenum 104 has four sections: superior, descending, transverse and ascending which typically form a U-shape. The superior section is about two inches long and ends at the neck of the gall bladder. The superior section also defines a feature referred to as the duodenal bulb 119 that begins just distal to the pylorus 108 and extends for about 1 to 1.5 inches (25 to 40 mm) in an adult human. The duodenal bulb 119 defines a lumen therein that is slightly larger than the distal duodenum 104. Advantageously, the duodenal bulb 119 exhibits less motion than the pylorus 108 and even distal portions of the duodenum 104. Notably, the motion is substantially limited to contractions without having a significant linear component (i.e., no movement along the central axis of the intestine). However, the tissue thins as one moves away from the pylorus 108.

The descending section of the duodenum 104 is about three to four inches long and includes a nipple shaped structure (papilla of Vater) 114 through which pancreatic juice from the pancreas and bile produced by the liver and stored by the gall bladder enter the duodenum from the pancreatic and bile ducts. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. In normal adults, the duodenum operates at a nominal relaxed interior diameter of about 25 mm (1 inch), and can maximally expand to about 40-50 mm (about 1.5-2 inches). The digestive system is described in Gray's Anatomy ("Anatomy of the Human Body," by Henry Gray) and "Human Physiology," Vander, $3^{rd}$ ed, McGraw Hill, 1980, the contents of which are incorporated herein by reference in their entirety.

Figure 1B:
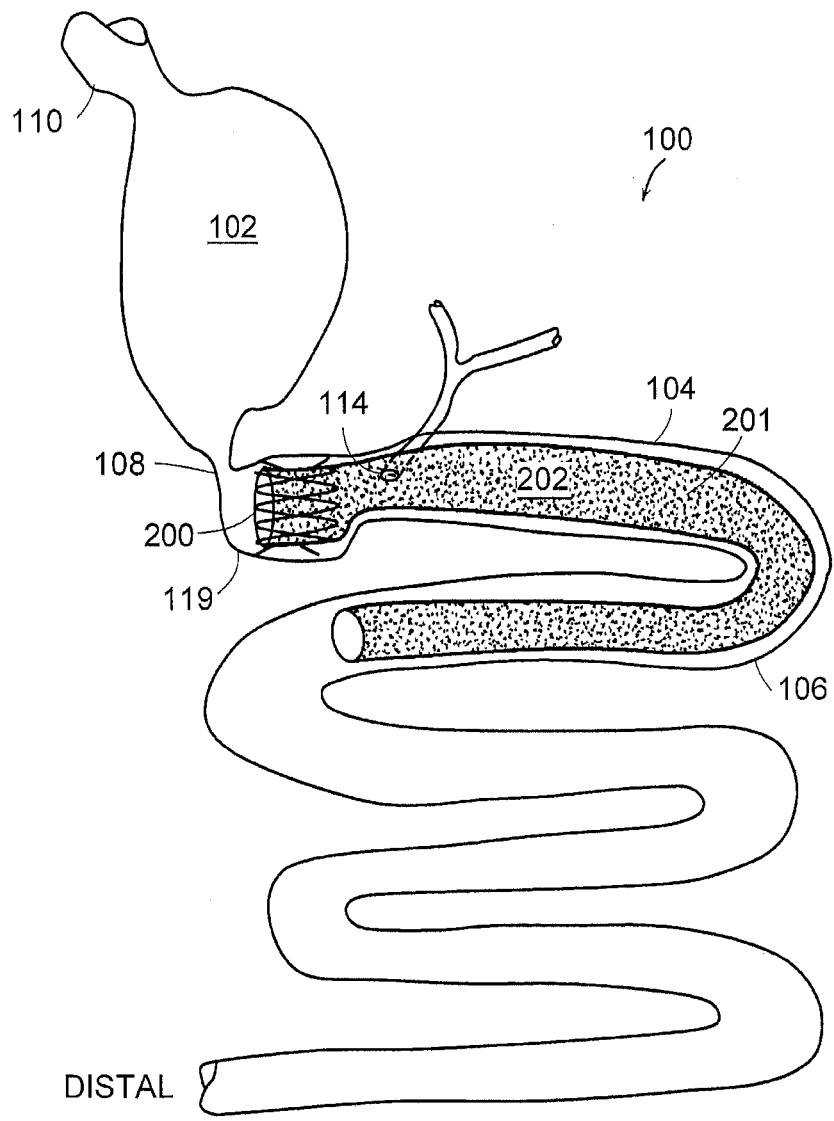
FIG. 1B is a drawing of a digestive tract with a gastrointestinal implant device 201 (including gastrointestinal anchor 200 and floppy sleeve 202) implanted in a subject.

FIG. 1B is a drawing of a digestive tract with a gastrointestinal implant device 201 (including gastrointestinal anchor 200 and floppy sleeve 202) implanted in a subject. When implanted, the central axis of the anchor 200 can be substantially aligned with the central axis of the duodenum 104, which can allow chyme to pass through the device 201. The sleeve 202 can extend over the ligament of Treitz 118 beyond the proximal jejunum 106. Extending the sleeve 202 below the ligament of Treitz 118 can reduce the likelihood that the sleeve 202 will move back through the duodenum 104 toward the stomach 102.

After the gastrointestinal implant device 200 has been placed in the body and anchored in the duodenum 104, chyme leaving the stomach can pass through sleeve 202 and bypasses the duodenum 104 and proximal jejunum 106. By directing the chyme through the sleeve 202 the digestion and the absorption process in the duodenum 104 can be interrupted. By interrupting mixing of the chyme with juices in the duodenum 104, partially digested food material is typically not broken down into particles small enough to be absorbed by the body. Further, there is typically no mixing of bile with the chyme until the chyme reaches the jejunum 106. The absorption of fats and carbohydrates can be reduced by delaying the mixing of bile with the chyme.

The sleeve 202 can provide weight loss mechanisms by providing negative feedback, reduced fat digestion and reduced desire for food. The reduced fat digestion can occur because the sleeve 202 can delay the mixing of bile and pancreatic juices with chyme from the stomach until after the chyme leaves the sleeve 202. The reduced desire for food may occur because the sleeve 202 blocks hormonal release from the duodenum 104. Additionally, providing poorly digested food to distal portions of the intestine, such as to the ileum, can trigger hormones that reduce appetite.

The sleeve 202 can drape away from the intestinal walls thereby permitting the pancreatic juice to flow unimpeded into the duodenum 104 through the papilla of Vater 114. The normal peristalsis of the bowel can be used to propel the chyme, bile, and pancreatic juices through the intestines.

Figure 1C:
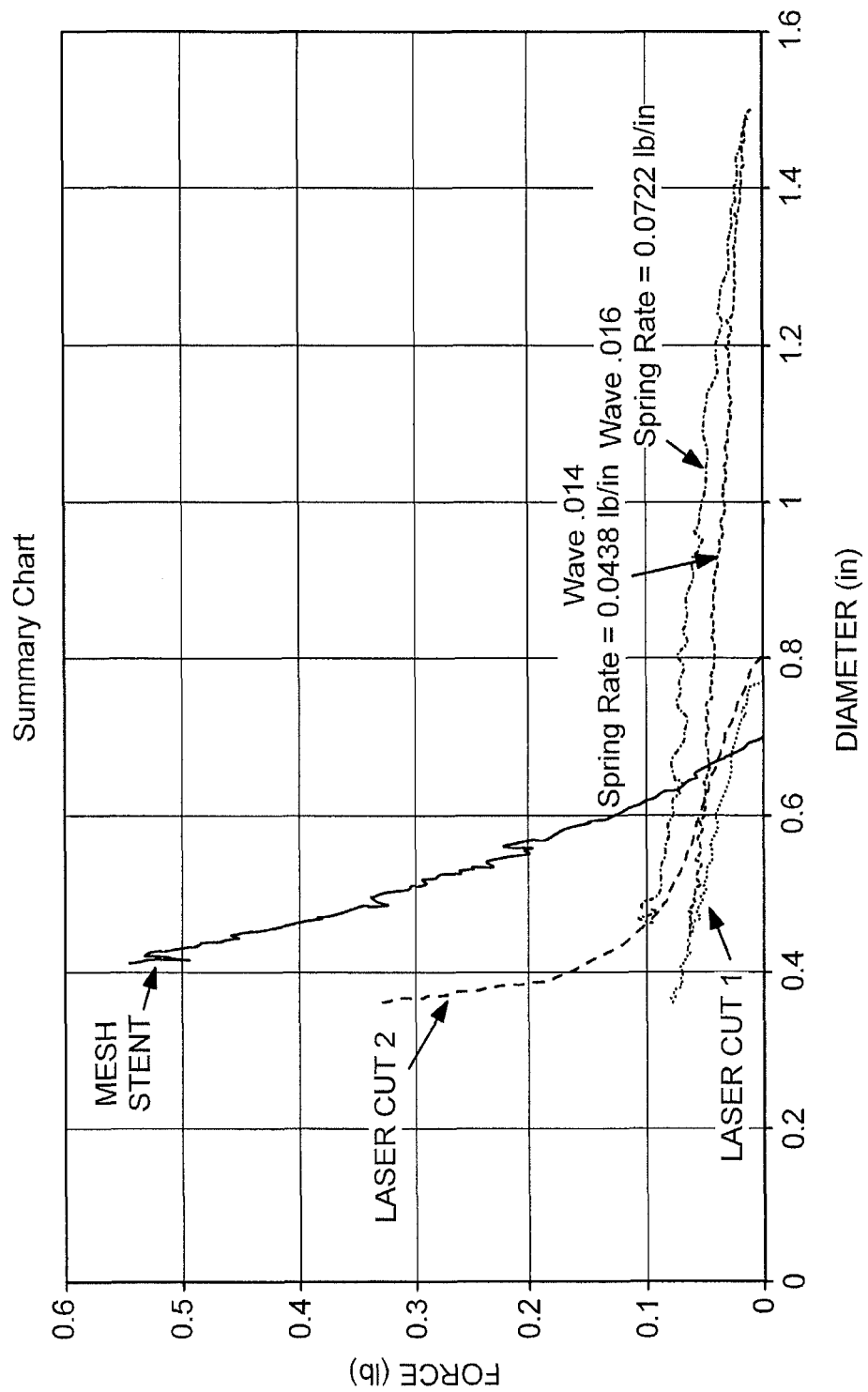
FIG. 1C is a graph of force versus displacement data for various anchor devices during loading (compression)

FIG. 1C is a graph of force versus displacement data for various anchor devices during loading (compression). Table 1 (below) shows the results. These mesh and laser cut stents have been used as stents for esophageal tumors. Stents cut from Nitinol tubing ("Laser cut 1" and "Laser cut 2") have a range of motion of about 0.45 inches (about 11 mm), and a maximum relaxed diameter of about 0.8 inches (about 20 mm). Another example, "Mesh stent" has a range of motion of about 0.3 inches (about 8 mm) and a maximum relaxed diameter of about 0.7 inches (about 18 mm) Made for esophageal tumors, these values are not sufficient to anchor the nominal relaxed interior diameter of the adult duodenum, which is about 25 mm, nor its normal range of motion, which is about 25 to 40 mm.

Wave anchors were presented by applicants for the purpose of anchoring a sleeve in the intestine. Two wave anchors ("Wave 0.014" and "Wave 0.016") have ranges of motion of about 1 inch (about 25 mm) and relaxed diameters of about 1.5 inches (about 38 mm), and can thus begin to address the diameter and range of motion of the intestine. Their spring rates are 0.0438 pounds/inch and 0.0722 pounds/inch (about 7.7 N/m and 12.6 N/m, respectively) and the force exerted by each (during loading) at 1 inch (25 mm), the nominal relaxed diameter of the duodenum, is 0.05 pounds and 0.04 pounds (about 0.2 N/m and about 0.16 N/m, respectively). (Force measurements have been made in pounds force. Conversion to metric units includes pounds force*4.448=Newtons force; pounds force/inch*175.1=Newtons/meter; 1 inch=25.4 mm). Moreover, while there is at present no known upper limit for radial force and spring rate in the intestine, it is believed that these lower radial forces, lower spring rates, and longer ranges of motion of these wave springs can allow for more natural motion in the intestine compared with the anchors in the preceding paragraph. It is believed that allowing the anchor to follow the natural motion of the intestine may provide more secure anchoring, may allow for better digestive system function and may tend to avoid subject discomfort. Thus, these wave spring anchors are believed to be superior to the anchors in the preceding paragraph. However, in experiments it was noted that these anchors tended to migrate in the duodenum.

TABLE 1

Test Results

|  | Mesh-type Stent | Wave-0.014 | Wave-0.016 | Laser-cut 1 | Laser-cut 2 |
| --- | --- | --- | --- | --- | --- |
| Spring Rate (lbs./inch): | 1.714 | 0.0438 | 0.0722 | 0.168 (long) 0.240 (short) | 0.253 |
| Approx. Range (inches): | 0.3 | 1.0 | 1.0 | 0.5 | 0.35 |

In contrast to the wave anchors above, multiple anchor characteristics have now been determined which lead to an improved ability to secure the anchor in the intestine. For example, an anchor should exert sufficient radial force against duodenum 104 to secure it in place, e.g., sufficient force to engage barbs on the anchor. Moreover, as the intestine naturally expands and contracts as a result of peristalsis, gas pressure, chyme movement, and the like, the anchor should be able to provide this sufficient force over the range of motion and diameter of the intestine. At the same time, it is believed that the radial force should have a sufficient spring rate so the radial force decreases as the diameter increases and the anchor does not tend to cause the intestine to expand or grow beyond its normal range. Also, the anchor should be reversibly collapsible for ease of implantation and removal; thus, any compressive elastic deformation diameter should be below the collapsed diameter employed for implantation.

It is believed that the stiffness of the anchor, or its compliance, can determine the ability of the device to both seal against the tissue, and also to maintain any attaching means, e.g., barbs engaged in the tissue. Both are important attributes to the function of the anchor. Also, the anchor should be sufficiently elastic to permit loading and delivery in a small capsule (max OD of 16 mm, practical ID of 12 mm) for implantation, followed by full expansion into the intestine. The diameter of the device should also be able to accommodate the full natural dilation of the tissue which we believe to be around 40-50 mm in the human.

If the compliance of the anchor is too high (too soft), the anchor may separate from the tissue and cause leaks and also migrations. If the anchor compliance is too low (too stiff), it may cause more irritation to the tissue, but more importantly, it will require a larger capsule for delivery to avoid compressing beyond its elastic deformation diameter. Anchors made to expand to 60 mm diameter from 0.016" diameter Nitinol wire were found to be insufficiently stiff to prevent migration. 50 mm anchors made from wire of 0.018" diameter did not test well on bench testing of anchoring strength. The bench testing consists of loading the anchor with a sleeve attached into a 25 mm ID synthetic model of the intestine (The Chamberlain Group, Great Barrington, Mass.). The distal end of the sleeve is pulled. If the barbs disengage from the model, the device is deemed to be too soft. If the model tears, the device is sufficiently stiff.

FIGS. 2A and 2B show disclosed anchor 200 in axial and perspective views at a relaxed diameter 25, without compression. FIGS. 2C and 2D show anchor 200 in axial and perspective views at a compressed diameter 26. In FIG. 2A, anchor 200 defines a lumen 21, having a central axis 22. Applying a radial compression force in direction 23 collapses anchor 200 towards central axis 22 of lumen 21. Radial compression of the anchor is opposed by a restoring spring force that opposes compression in an outward radial direction 24 extending from central axis 22. This force should be sufficient to secure anchor 200 in place against duodenum 104. For example, in FIG. 1C, the radial force at 25 mm of the two wave springs are about 0.05 pounds (0.2 N) or less, and in FIG. 3B, the radial force at 25 mm of the lowest curve is about 0.065 lbs (less than 0.3 N). Because these three examples exhibited migration, it is desirable in various embodiments that the anchor is characterized by a radial force of about 0.3 Newtons (N) or greater at a compressed diameter of 25 millimeters (mm). Typically, the radial force at 25 mm compression can be about 0.4 N or greater, or particularly between about 0.5 N and about 1.5 N.

Moreover, the anchor should be able to provide sufficient force over the range of motion of the intestine. In various examples (as will be explained in greater detail below for FIGS. 3A, 3B, and 4), it was determined that the nominal postoperative diameter tended to fall in a range where the loading radial force of the anchors at the top of the postoperative diameter range was between about 0.05 and about 0.1 pounds (from FIGS. 3A and 3B; about 0.2N and about 0.4 N). It is believed that this radial force range at these diameters is thus associated in pigs with a long-term steady state expansion value. It is desirable to provide at least these forces over the range of motion, but not to exceed these forces at the expanded diameter to avoid over expansion of the gastrointestinal tract at the location of the anchor. Thus, in various embodiments, anchor 200 is characterized by a radial force over the range of motion of about 0.2 N or greater, more typically, about 0.3 N or greater, or particularly about 0.4 N or greater.

The range of motion is located between the relaxed diameter of the anchor and a compressive elastic deformation diameter of the anchor. In various embodiments, the range of motion can occupy the entire distance between the relaxed diameter and the compressive elastic deformation limit, or the range of motion can occupy a subrange between the relaxed diameter and the compressive elastic deformation limit. The range of motion should be large enough to accommodate the natural range of motion of the intestine. Thus, in some embodiments, the range of motion can be about 20 mm or greater, more typically about 30 mm or greater, or particularly about 35 mm or greater. In some embodiments, the range of motion can be a percentage of the relaxed diameter of the anchor of about 30% or greater.

In various embodiments, the anchor is characterized by a relaxed diameter 25. As used herein, the "relaxed diameter" is the natural or equilibrium diameter of the anchor when the anchor is free of any external force. The relaxed diameter should be large enough to accommodate the natural range of diameter in the subject's intestine. Otherwise, if the intestine expanded beyond the relaxed diameter, the barbs or other attaching means could pull loose, allowing the anchor to migrate. Generally, the relaxed diameter can be about 40 mm or greater, typically, about 45 mm or greater, or more typically, between about 45 mm and about 65 mm. In particular embodiments, the relaxed diameter can be about 50 mm or about 60 mm.

As used herein, the "compressive elastic deformation diameter" is the limit of diameter compression below which the anchor deforms and will not return to its original relaxed diameter or original relaxed shape. The compressive elastic deformation diameter can be characterized in absolute or relative terms. Thus, in various embodiments, the compressive elastic deformation diameter is about 12 mm or less, or particularly about 8 mm or less. In various embodiments, the compressive elastic deformation diameter is a percentage of the relaxed diameter of about 30% or less, more typically about 20% or less.

In various embodiments, anchor 200 can be characterized by an average spring rate over the range of motion. For example, in FIG. 2A, anchor 200 is compressed from a relaxed diameter 25 to a compressed diameter 26, and the radial restoring force 24 can be divided by the difference between relaxed diameter 25 and compressed diameter 26 to give a spring rate. Thus, for an anchor with a relaxed diameter of 60 mm and a force of 0.4 N at a compressed diameter of 25 mm can be calculated to have a spring rate of 0.4/(60–25)=13 N/m. Also, the average spring rate can also be calculated by recording compression force versus compression distance data and performing standard least squares analysis to obtain the average value of the force/distance slope, corresponding to the spring rate (N/m). Thus, in various embodiments, the anchor is characterized by an average spring rate of about 13 Newtons/meter (N/m) or greater in a range of motion, the range of motion being within a diameter range defined by a relaxed diameter and a compressive elastic deformation diameter. More particularly, the average value of the spring rate is between about 15 N/m and about 35 N/m.

Figure 3A:
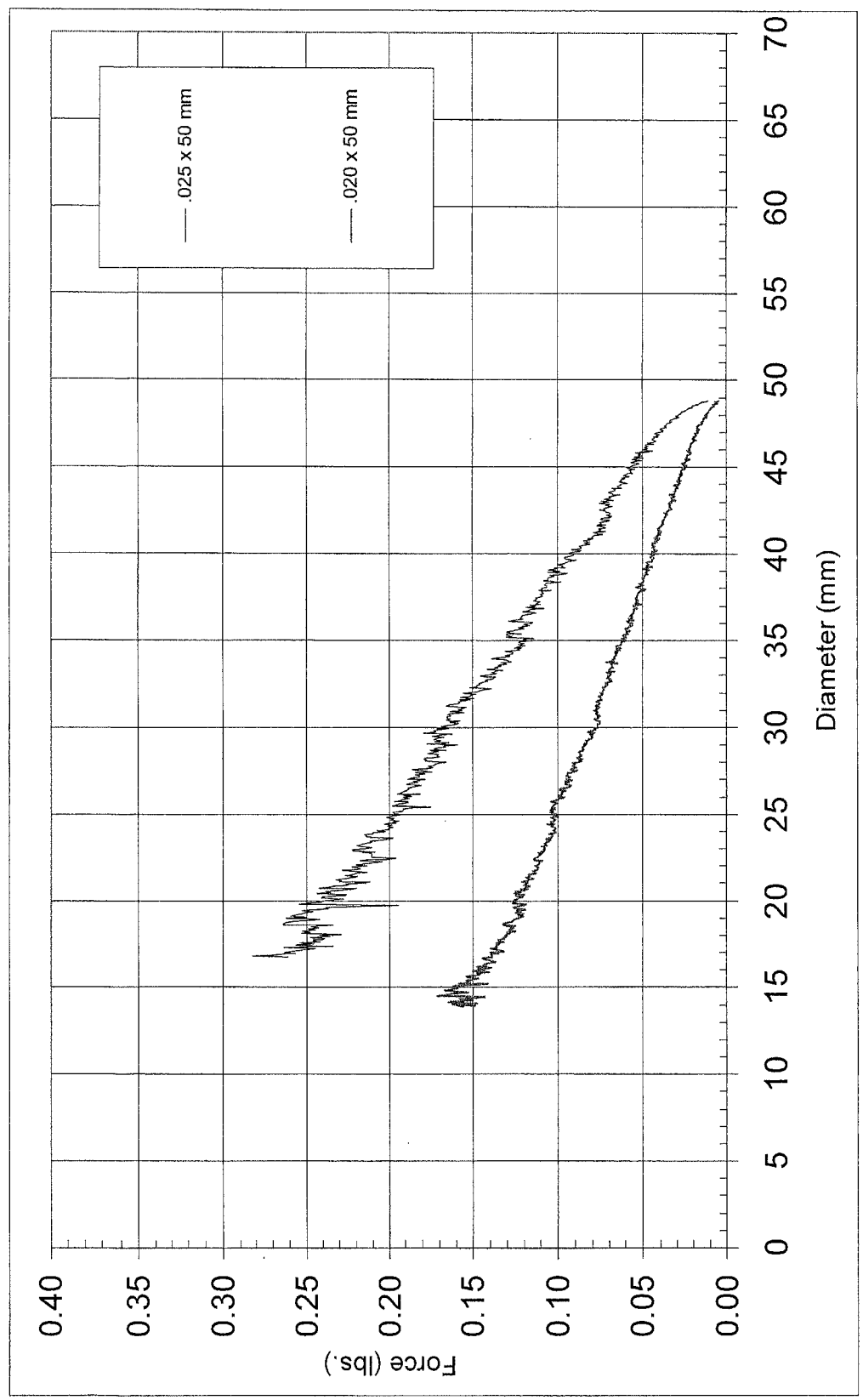
FIGS. 3A and 3B are graphs of exemplary compliance curves for various 50 mm (FIG. 3A) and 60 mm (FIG. 3B) anchors of the invention during loading (compression)
Figure 3B:
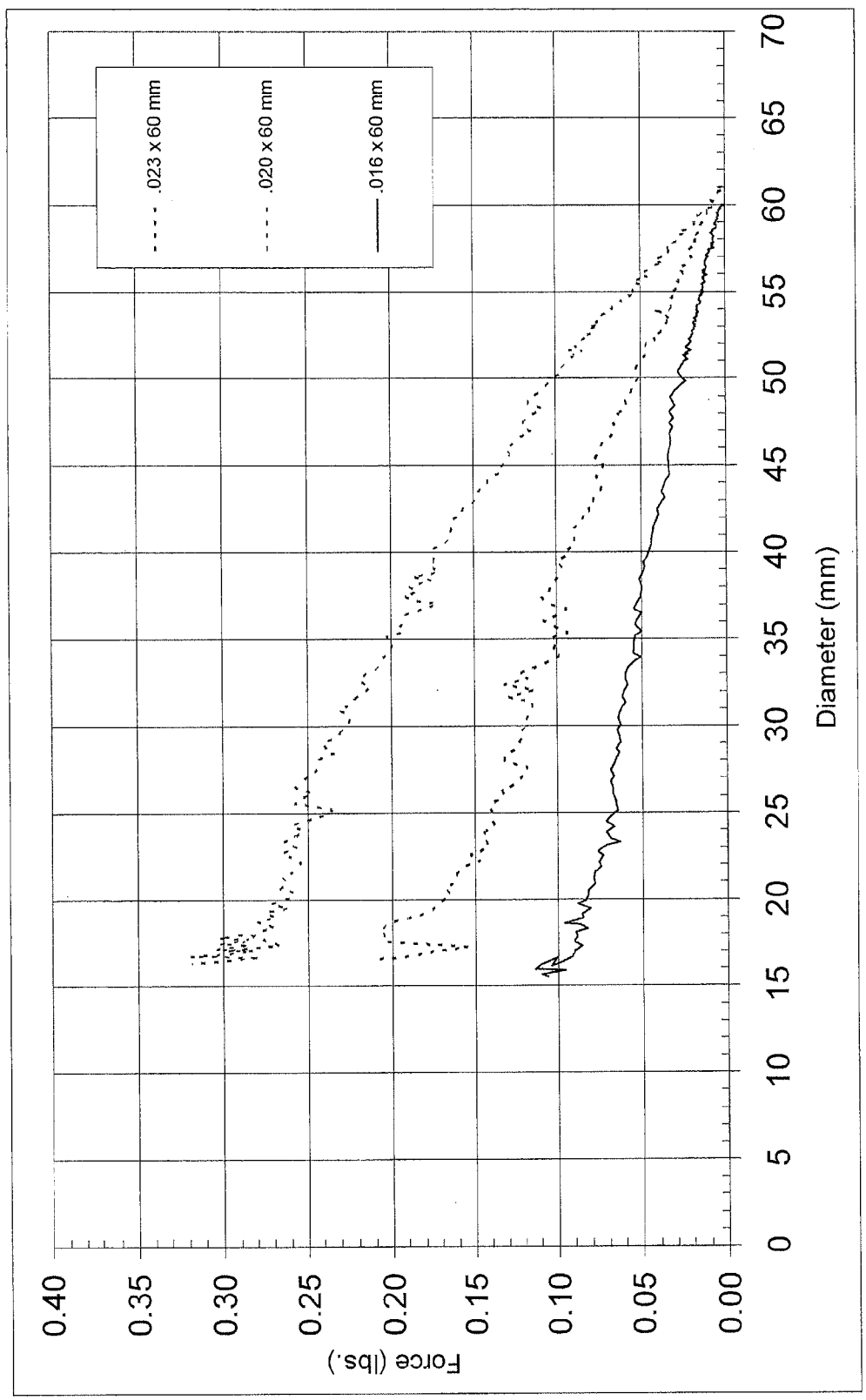

Anchors up to 60 mm diameter have been fabricated from 0.023" Nitinol wire. The curves in FIGS. 3A and 3B show the compliance of various anchors. The wire diameter of the anchor can be adjusted to provide the desired force. Typically, shorter anchors use thinner wires. For example, a 19 mm long anchor was made from 0.016" diameter wire to provide the same compliance as the 32 mm long anchors shown in FIGS. 3A and 3B. As the diameter of the wire becomes larger, the compressive elastic deformation diameter increases, so thicker wire can limit the ability of the anchor to pack into a 12 mm capsule for delivery without deformation. The curves in FIGS. 3A and 3B were measured on bare anchors. When covered with sleeve material, the curves move up slightly (become stiffer). However, over time, the sleeve material softens so it is believed to have a minimal effect on compliance.

FIG. 3A shows curves during loading (compression) for two disclosed wave anchors having relaxed diameters of 50 mm. The lower curve has a radial force at 25 mm compression of about 0.1 pounds (about 0.4 N), a radial force at 40 mm of about 0.05 pounds (about 0.2 N), and a substantially linear spring rate of about 18.5 N/m over a range of motion of almost 35 mm. The upper curve has a radial force at 25 mm compression of about 0.2 pounds (about 0.8 N), a radial force at 45 mm of about 0.06 pounds (about 0.24 N), and a substantially linear spring rate of about 32 N/m over a range of motion of almost 35 mm. Another anchor (curve not shown) was constructed with a radial force at 25 mm compression of about 0.18 pounds (about 0.8 N) and other characteristics similar to the upper curve. Upon implantation into pigs, it was found that these 50 mm anchors were secure and did not migrate.

FIG. 4 is a plot of anchor diameter, measured from X-ray images of the implanted anchors, versus days after implantation for 50 mm and 60 mm anchors implanted in pigs. FIG. 4 shows that the diameter of the 50 mm anchors in pigs tended towards a range of 30 to 40 mm. Thus, these anchors were able to accommodate the range of motion in the intestine within their 50 mm relaxed diameters.

FIG. 3B shows curves during loading (compression) for three wave anchors having relaxed diameters of 60 mm. The lower curve has a radial force at 25 mm compression of less than 0.07 pounds (less than 0.3 N), a radial force at 40 mm of less than 0.05 pounds (about 0.2 N), and a substantially linear spring rate of about 10 N/m over a range of motion of almost 45 mm. The middle curve has a radial force at 25 mm compression of about 0.14 pounds (about 0.6 N), a radial force at 50 mm of about 0.05 pounds (about 0.2 N), and a substantially linear spring rate of about 18 N/m over a range of motion of almost 45 mm. The upper curve has a radial force at 25 mm compression of about 0.25 pounds (about 1.1 N), a radial force at 55 mm of about 0.05 pounds (about 0.2 N), and a substantially linear spring rate of about 30 N/m over a range of motion of almost 45 mm. Upon implantation into pigs, it was found that these 60 mm anchors were effective, though only the anchors represented by the middle and upper curves were secure and did not migrate.

Figure 4A:
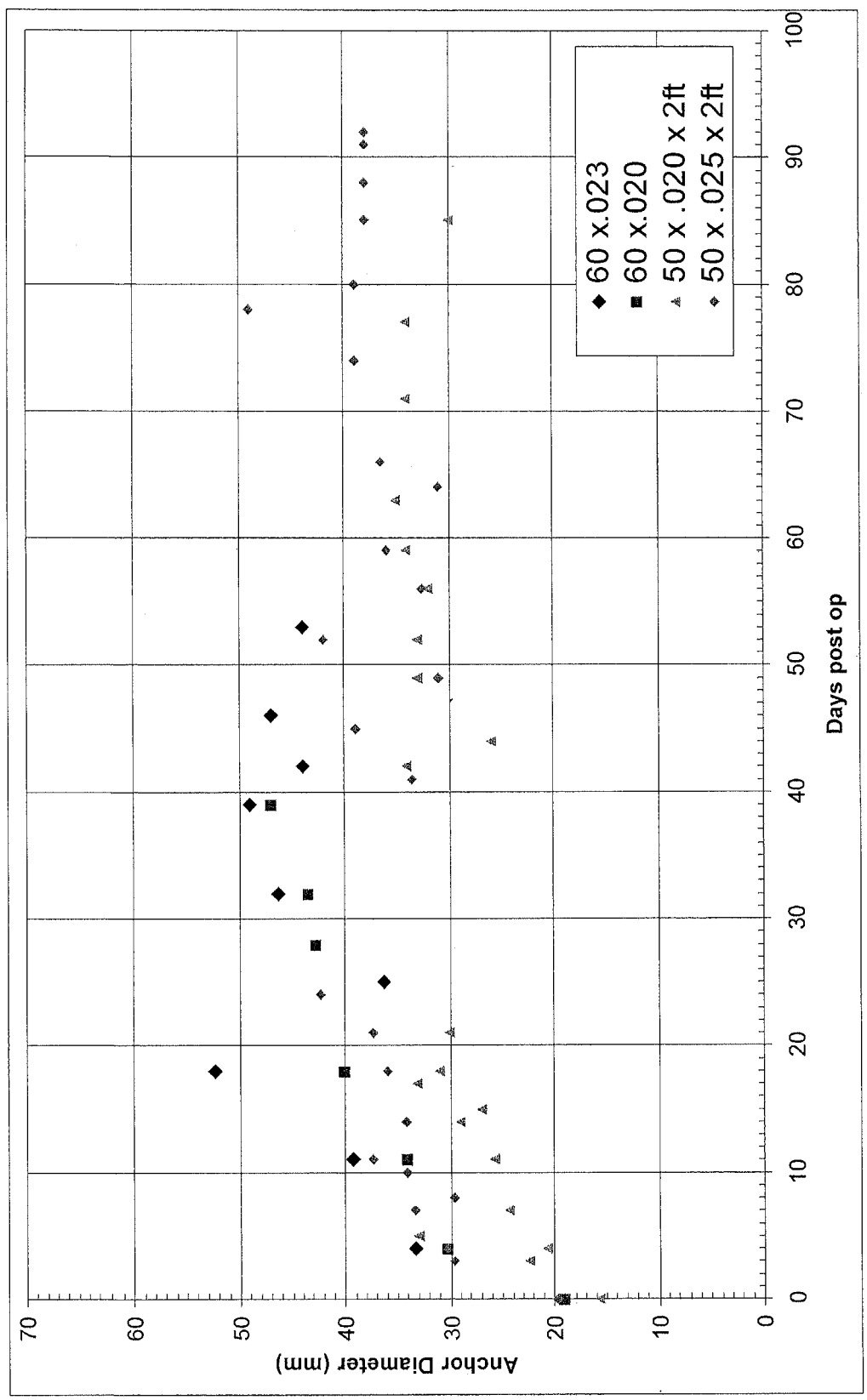
FIG. 4A is a plot of anchor diameter, measured from X-ray images of the implanted anchors, versus days post operation for 50 mm and 60 mm anchors implanted in pigs.

FIG. 4A shows that the diameter of two of the 60 mm anchors when implanted in pigs (measured from X-ray images of the implanted anchors) tended towards a range of 40 to 50 mm. Thus, these anchors were able to accommodate the range of motion in the intestine within their 60 mm relaxed diameters.

It can be seen in FIG. 4 that for the 50 mm and 60 mm anchors that were followed by X-ray, the nominal postoperative diameter tended to fall in a range where the radial force of the anchors at the top end of the respective ranges was between about 0.05 and about 0.1 pounds (from FIGS. 3A and 3B; about 0.2N and about 0.4 N). For example, for the 50 mm anchors, the nominal postoperative diameter was about 30 to about 40 mm and the radial force of the anchors at 40 mm was between about 0.05 and about 0.1 pounds (from FIG. 3A; about 0.2N and about 0.4 N). For the 60 mm anchors, the nominal postoperative diameter was about 40 to about 50 mm and the radial force of the anchors at 50 mm was between about 0.05 and about 0.1 pounds (from FIG. 3B; about 0.2N and about 0.4 N). It is believed that this radial force range at these diameters is thus associated in pigs with a long-term steady state expansion value. It is desirable to not exceed these forces at the expanded diameter to avoid over expansion of the gastrointestinal tract at the location of the anchor.

Thus, in various embodiments, the anchor can be characterized by the radial force being about 0.4 N or less at a diameter of 55 mm, typically at a diameter of 50 mm, more typically at a diameter of 45 mm, or particularly at a diameter of 40 mm. In various embodiments, the anchor can be characterized by the radial force being about 0.3 N or less at a diameter of 55 mm, typically at a diameter of 50 mm, more typically at a diameter of 45 mm, or particularly at a diameter of 40 mm. In various embodiments, the anchor can be characterized by the radial force being about 0.2 N or less at a diameter of 55 mm, typically at a diameter of 50 mm, more typically at a diameter of 45 mm, or particularly at a diameter of 40 mm.

Figure 4C:
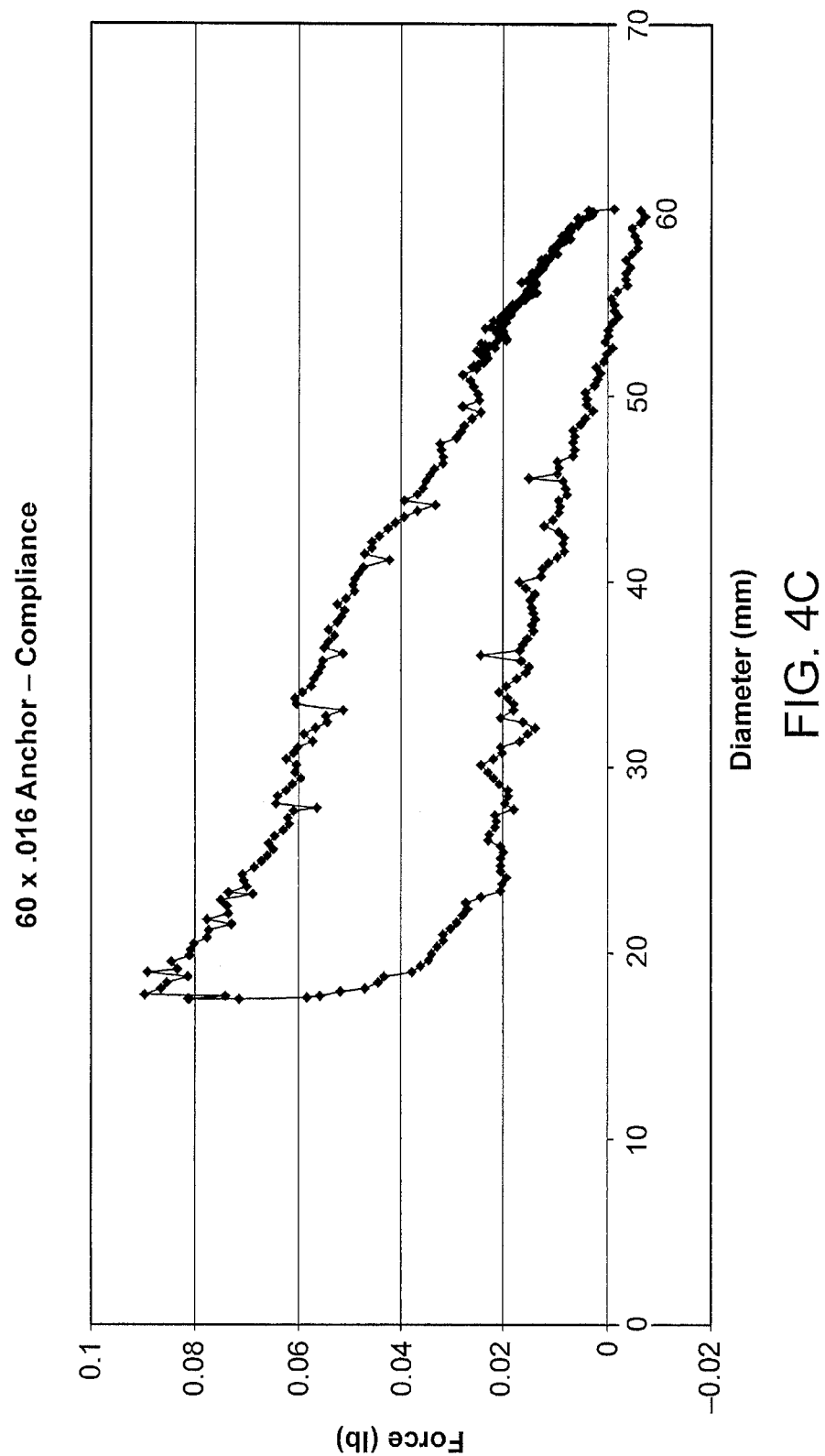
FIG. 4C is a hysteresis plot of another 50 mm diameter by 0.023 inch thick Nitinol wave anchor.
Figure 4D:
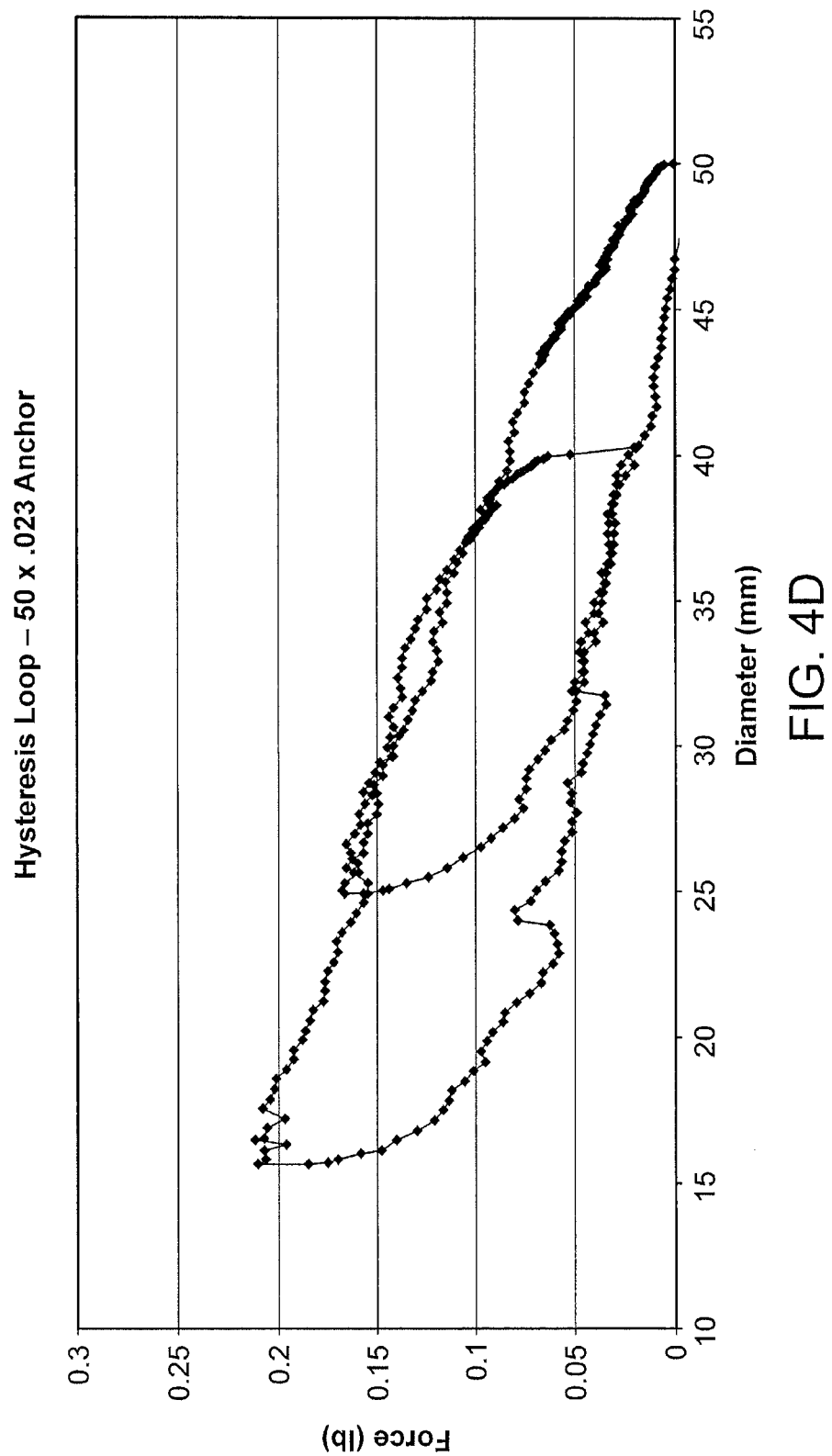
FIG. 4D is a hysteresis plot of a 60 mm diameter by 0.016 inch thick Nitinol wave anchor.

FIGS. 4B, 4C, and 4D show hysteresis curves of the anchors. The top portion of each curve represents the radial force values recorded during compression from the relaxed diameter (also known as loading), and the bottom portion represents the radial force measured during expansion (also known as unloading). It can be seen, for example, that the radial force value at 25 mm for the same spring can be about 0.07 to about 0.02 pounds (FIG. 4B, about 0.3 N to about 0.09 N) 0.16 to about 0.06 pounds (FIG. 4C, 0.7 to about 0.3 N) and about 0.18 to about 0.08 pounds (FIG. 4D, 0.8 to about 0.4 N). It is believed that the important force at any condition is the minimum force. Thus, in some embodiments, the radial force measured at 25 mm is about 0.1 N or greater. In some embodiments, the radial force is at least about 0.1 N over a range of motion of about 20 mm, the range of motion being between the relaxed diameter and the compressive elastic deformation diameter.

The preceding examples were performed on pigs sized to have intestines approximately representative of intestines in adult humans. Thus, it is believed that one of ordinary skill in the art can use or adapt the values of the characteristics described herein for use in human subjects, taking into account the size and medical history of a particular subject, and if necessary, evaluating the results in the subject in light of the examples and values disclosed herein.

In various embodiments, the anchor can be in the form of a ring, a stent formed by a network of struts, or a wave spring. Typically the anchor can be a wave spring.

Figure 5A:
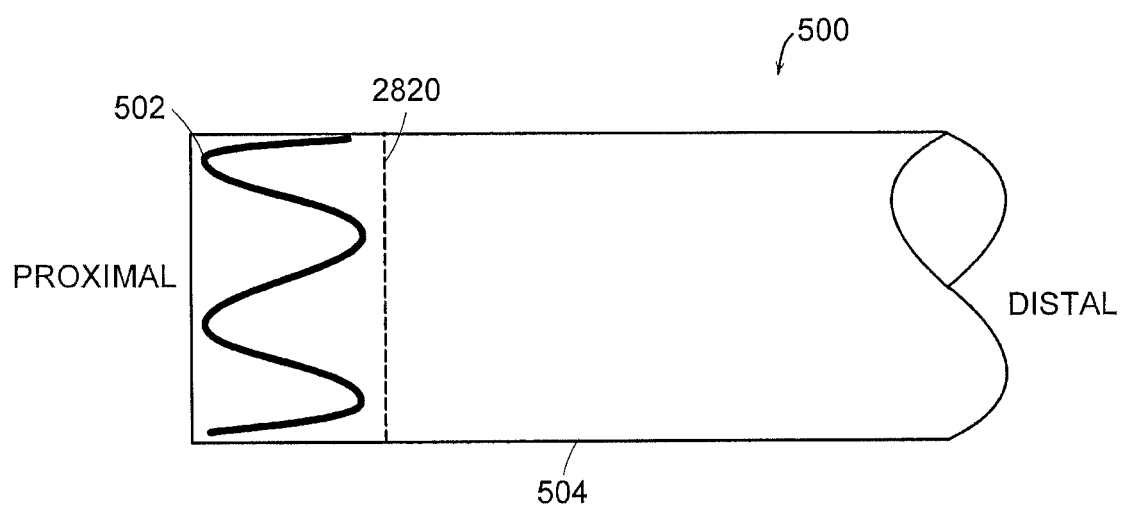
FIG. 5A is a perspective view of a collapsible self-expanding wave anchor coupled to the proximal portion of a sleeve to form a gastrointestinal implant device.

FIG. 5A is a perspective view of a gastrointestinal implant device 500 for implantation in the duodenum 104. A collapsible self-expanding wave spring 502 (an embodiment of anchor 200 in FIGS. 2A-2D) is coupled to a proximal portion of a sleeve 504.

Figure 5B:
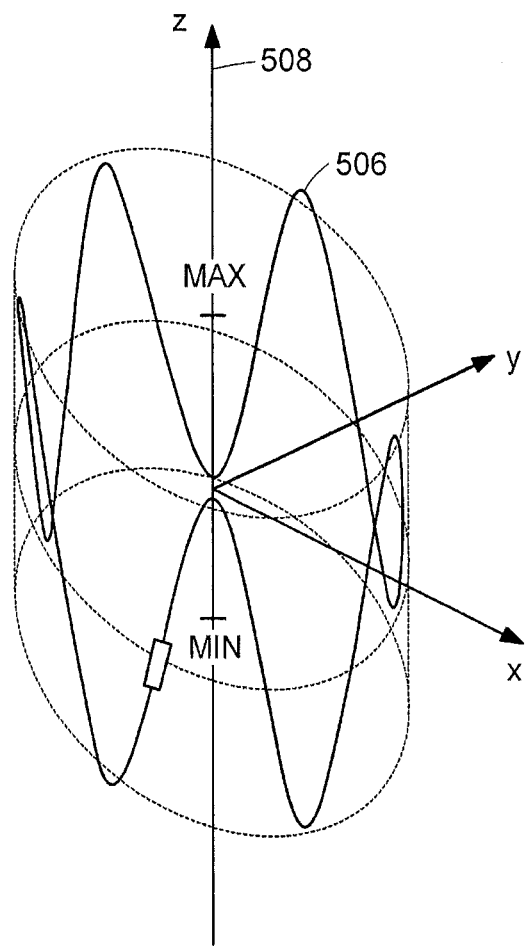
FIG. 5B is a detail drawing of the wave anchor of FIG. 5A.

FIG. 5B is a detailed drawing of the wave anchor 502, which includes a compliant, radial spring 506 shaped into an annular wave pattern about a central axis 508, providing an outward radial force, while allowing substantial flexure about its perimeter. Such flexure is advantageous as it allows for minimally-invasive delivery and ensures that the device will substantially conform to the surrounding anatomical structure when implanted. The annular wave element 2900 can be formed from one or more elongated resilient members and defines a lumen along its central axis formed between two open ends.

The disclosed anchor, e.g., compliant wave anchor 502, can be manufactured from a resilient metal such as a heat-treated spring steel, stainless steel, or from an alloy such as NiTi alloy commonly referred to as Nitinol. Other alloys include nickel-cobalt-chromium-molybdenum alloys possessing a unique combination of ultrahigh tensile strength, such as MP35N. Additionally, the anchor can be formed from a polymer and/or a composite having similar properties. The anchor can be manufactured from a single strand, such as a wire, contoured into the desired shape. Alternatively, the disclosed anchor can be manufactured from multi-strands of the same or different materials similarly contoured to the desired shape. In some embodiments, the wave anchor 502 can be cut into the wave shape from tubular stock of the desired material, such as Nitinol.

An advantage of the disclosed anchors is the ability to form an anchor having a appropriate radial force values over a very long range of diameters in contrast to mesh-type stents and stents cut from Nitinol tubing ("Mesh stent" "Laser cut 1" and Laser cut 2" in FIG. 1C). The disclosed anchors operate over a longer range of diameters in contrast to the mesh type stents, and have appropriate radial force and spring rate values to secure the anchors, in contrast to the wave type anchors.

In various embodiments, the anchor includes attaching means adapted to secure the anchor to the intestine. The attaching means can include an interference fit, chemical fasteners, mechanical fasteners, or the like. For example, the anchor can be attached to the surrounding anatomy using an interference fit provided by the relative size of the anchor in relation to the surrounding anatomy. Alternatively or in addition, the anchor can be attached to the surrounding anatomy using chemical fasteners, such as surgical adhesives. Mechanical fasteners can include, for example, sutures, surgical staples, barbs, or the like. In some embodiments, the mechanical fasteners can be dissolvable, dissolving after a predetermined time and allowing the device to pass naturally. Mechanical fasteners can include barbs that extend from the exterior surface of the anchor for anchoring the proximal portion of the sleeve to the muscular tissue of the surrounding anatomy. The barbs may be bi-directional for anchoring the proximal portion of the flexible sleeve to the intestine. Typically, the barbs are bi-directional and are aligned with the peristaltic axis of the gastrointestinal tract, i.e., some barbs are pointed in the direction of forward peristalsis to secure the anchor against forward motion through the gastrointestinal tract, and some barbs are pointed opposite the direction of forward peristalsis, to secure the anchor against reverse motion in the gastrointestinal tract. Typically, the barbs secure the anchor to muscular tissue of the intestine. In various embodiments, the barbs extend from the surface exterior surface of the anchor by about 2 mm or greater. In various embodiments, the method includes securing the proximal portion of the sleeve to the intestine in the subject with the barbs.

Figure 6:
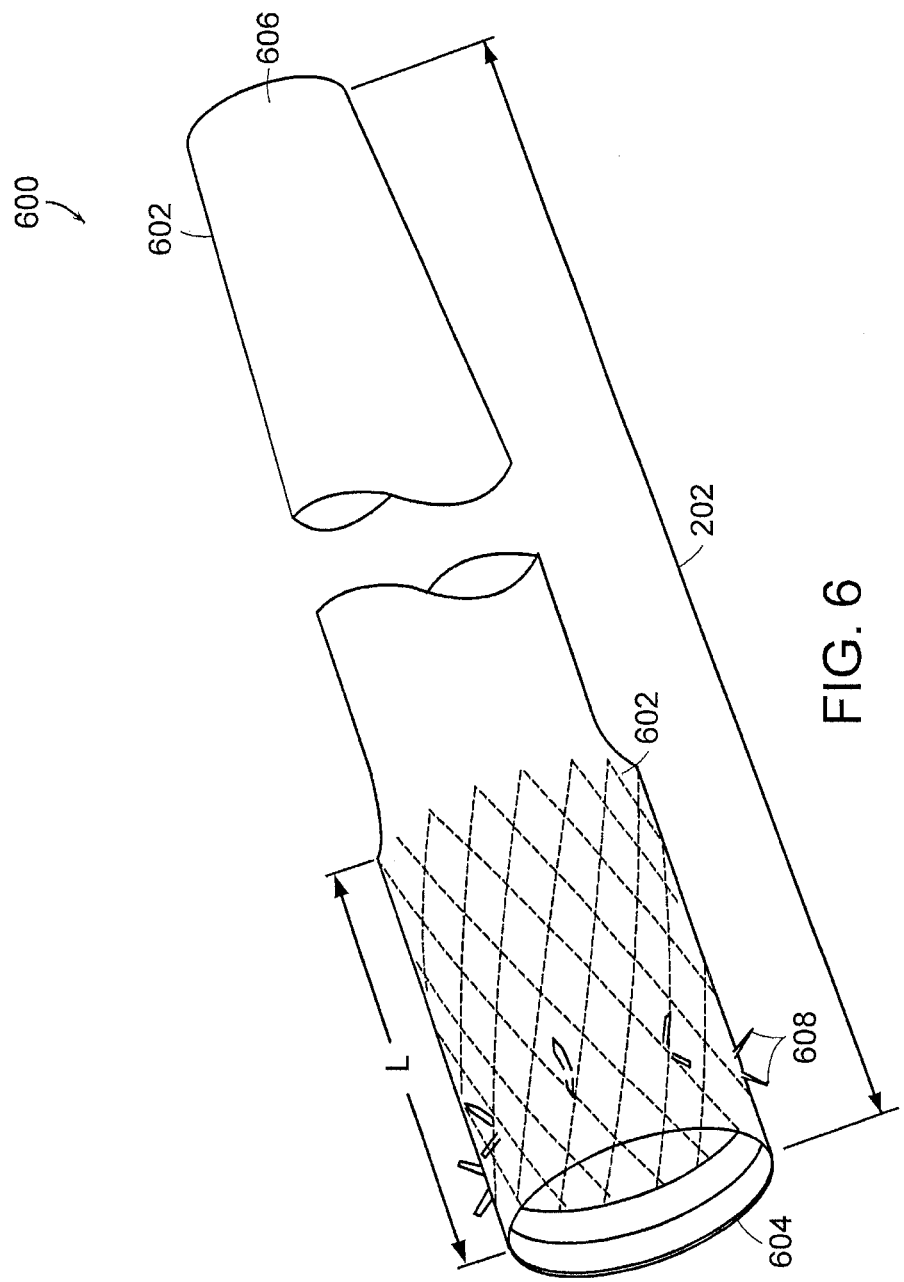
FIG. 6 is a perspective view of a collapsible self-expanding stent anchor coupled to the proximal portion of a sleeve to form a gastrointestinal implant device, the stent comprising barbs.

FIG. 6 is a perspective view of a gastrointestinal implant device 600 according to the principles of the present invention showing attaching means as barbs 608. The gastrointestinal implant device 600 includes an elongated, open-ended, unsupported flexible sleeve or tube 604 having a first proximal opening 606 and a second distal opening 608. Within the sleeve 604 is a passageway that extends from the first proximal opening 606 to the second distal opening 608 for transporting the chyme exiting the stomach 102 (FIG. 1). The surface of the passageway (the interior surface of the implant device 600) is smooth to enable the chyme to easily pass through. The exterior surface of the implant device 600 is smooth to prevent tissue in-growth and to be non-irritating to the bowel.

Within the implant device 600 at the proximal end including the first proximal opening 606 is a collapsible self-expanding anchor 602 in the form of a stent (e.g., an embodiment of anchor 200 in FIG. 2A-2D). The anchor 602 can include a plurality of opposed barbs 608 for anchoring the implant device 600 to the muscular tissue of the duodenum 104. The diameter of the anchor 602 is dependent on the diameter of the duodenum 104 (FIG. 1) about 1.0" to 2.5" (about 25 mm to about 65 mm) based on human anatomy variations. In one embodiment, the length 'l' of the anchor 602 is selected to reside within the bulbous duodenum 119.

Further examples of methods and apparatus for implanting the anchors and devices of the invention, anti-bucking devices, methods of treatment, details of construction of the anchors, sleeves, impregnation of the sleeves with drugs for treatment of various conditions, and the like are provided in Meade et al U.S. Utility application Ser. No. 10/858,851, filed Jun. 1, 2004; Levine, et al, U.S. Provisional Patent Application Ser. No. 60/611,038; filed: Sep. 17, 2004; Levine, et al, U.S. Provisional Patent Application Ser. No. 60/645,296; filed: Jan. 19, 2005; and DiCesare, et al U.S. Provisional Patent Application Ser. No. 60/645,287, filed: Jan. 19, 2005. The entire teachings of these documents are incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A gastrointestinal implant device comprising:
    a flexible sleeve, open at both ends and adapted to extend into a subject's intestine; and
    a collapsible gastrointestinal anchor, coupled to a proximal portion of the sleeve and characterized by an average spring rate of between about 13 Newtons/meter (N/m) and about 35 N/m in a range of motion of about 20 mm or greater, the range of motion being within a diameter range defined by a relaxed diameter and a compressive elastic deformation diameter.

2. The gastrointestinal implant device of claim 1, the spring rate being the spring rate while the anchor is unloaded from a compressed state.

3. The gastrointestinal implant device of claim 1, characterized by a relaxed diameter of about 40 mm or greater.

4. The gastrointestinal implant device of claim 1, the average value of the spring rate being between about 15 N/m and about 35 N/m.

5. The gastrointestinal implant device of claim 1, the range of motion being about 30 mm or greater.

6. A method of treating a subject, comprising the steps of:
    securing a gastrointestinal implant device within a subject's intestine, the device including a flexible sleeve, open at both ends and adapted to extend into the subject's intestine; and a collapsible gastrointestinal anchor, coupled to a proximal portion of the sleeve and characterized by an average spring rate of between about 13 Newtons/meter (N/m) and about 35 N/m in a range of motion of about 20 mm or greater, the range of motion being within a diameter range defined by a relaxed diameter and a compressive elastic deformation diameter; and extending the distal end of the sleeve into the subject's intestine.

7. The method of claim 6, the anchor being characterized by a relaxed diameter of about 40 mm or greater.

8. The method of claim 6, the average value of the spring rate being between about 15 N/m and about 35 N/m.

9. The method of claim 6, the range of motion being about 30 mm or greater.

10. A collapsible gastrointestinal anchor comprising a wave spring having a plurality of barbs extending therefrom, the wave spring being characterized by:

a relaxed diameter of about 40 millimeters (mm) or greater;

a compressive elastic deformation diameter of about 12 mm or less;

an average spring rate of between about 13 Newtons/meter (N/m) and about 35 N/m over a range of motion of about 20 mm or greater, the range of motion being within a diameter range defined by the relaxed diameter and the compressive elastic deformation diameter; and a radial force under compression, the radial force being between about 0.1 Newtons (N) and about 1.5 N at a diameter of 25 mm, and the radial force being between about 0.1 N and about 1.5 N over the range of motion, the spring rate and the radial force being the spring rate and the radial force while the spring is unloaded from a compressed state.

11. A gastrointestinal implant device comprising:

a flexible sleeve, open at both ends and adapted to extend into a subject's intestine; and a collapsible gastrointestinal anchor coupled to a proximal portion of the sleeve, the anchor comprising a wave spring having a plurality of barbs extending therefrom, the wave spring being characterized by a relaxed diameter of about 40 millimeters (mm) or greater; a compressive elastic deformation diameter of about 12 mm or less; an average spring rate of between about 13 Newtons/meter (N/m) and about 35 N/m over a range of motion of about 20 mm or greater, the range of motion being within a diameter range defined by the relaxed diameter and the compressive elastic deformation diameter; and a radial force under compression, the radial force being between about 0.1 Newtons (N) and about 1.5 N at a diameter of 25 mm, and the radial force being between about 0.1 N and about 1.5 N over the range of motion, the spring rate and the radial forces being the spring rate and the radial forces while the spring is unloaded from a compressed state.

12. A method of treating a subject, comprising the steps of:

securing a gastrointestinal implant device within a subject's intestine, the device including a flexible sleeve, the sleeve open at both ends and adapted to extend into the subject's intestine, and a collapsible gastrointestinal anchor coupled to a proximal portion of the sleeve, the anchor comprising a wave spring having a plurality of barbs extending therefrom; and extending the distal end of the sleeve into the subject's intestine, the wave spring being characterized by a relaxed diameter of about 40 millimeters (mm) or greater; a compressive elastic deformation diameter of about 12 mm or less; an average spring rate of between about 13 Newtons/meter (N/m) and about 35 N/m over a range of motion of about 20 mm or greater, the range of motion being within a diameter range defined by the relaxed diameter and the compressive elastic deformation diameter; and a radial force under compression, the radial force being between about 0.1 Newtons (N) and about 1.5 N at a diameter of 25 mm, and the radial force being between about 0.1 N and about 1.5 N over the range of motion, the spring rate and the radial forces being the spring rate and the radial forces while the spring is unloaded from a compressed state.

\* \* \* \* \*